United States Patent [19]

Maienfisch et al.

[11] Patent Number: 5,852,012
[45] Date of Patent: Dec. 22, 1998

[54] OXADIAZINE DERIVATIVES

[75] Inventors: Peter Maienfisch, Rodersdorf; Laurenz Gsell, Basel, both of Switzerland

[73] Assignee: Novartis Corporation, Summit, N.J.

[21] Appl. No.: 464,931

[22] Filed: Jun. 5, 1995

Related U.S. Application Data

[62] Division of Ser. No. 270,612, Jul. 5, 1994, abandoned, which is a division of Ser. No. 91,801, Jul. 14, 1993, abandoned.

[30] Foreign Application Priority Data

Jul. 22, 1992 [CH] Switzerland .................. 2315/92

[51] Int. Cl.$^6$ .................................................. A01N 43/88
[52] U.S. Cl. ........................ 514/229.2; 47/57.6; 47/58; 504/100; 544/67
[58] Field of Search ................. 544/67; 514/229.2; 47/57.6, 58; 504/100

[56] References Cited

U.S. PATENT DOCUMENTS

| | | | |
|---|---|---|---|
| 4,742,056 | 5/1988 | Farooq et al. | 514/229.2 |
| 4,803,277 | 2/1989 | Shiokawa et al. | 514/332 |
| 4,849,432 | 7/1989 | Shiokawa et al. | 514/341 |
| 4,880,933 | 11/1989 | Shiokawa et al. | 544/332 |
| 5,032,589 | 7/1991 | Shiokawa et al. | 514/245 |
| 5,034,404 | 7/1991 | Uneme et al. | 514/365 |
| 5,034,524 | 7/1991 | Shiokawa et al. | 544/124 |
| 5,051,434 | 9/1991 | Kozo et al. | 514/357 |
| 5,719,146 | 2/1998 | Shiokawa et al. | 514/229.2 |

FOREIGN PATENT DOCUMENTS

| | | |
|---|---|---|
| 0225854 | 6/1987 | European Pat. Off. . |
| 0230863 | 8/1987 | European Pat. Off. . |
| 0235725 | 9/1987 | European Pat. Off. . |
| 0277317 | 8/1988 | European Pat. Off. . |
| 0386565 | 9/1990 | European Pat. Off. . |
| 7-224062 | 8/1995 | Japan . |

OTHER PUBLICATIONS

Takimoto et al., Bull. Chem. Soc. Jpn., 56, pp. 3319–3322 (1983).
Shiba et al., Bull. Chem. Soc. Jpn., 62, pp. 3721–3723 (1989).
Yu et al., Chem. Abstracts 111:157006q (1989).
Yu et al, Propellante, Explosives, Pyrotechnics 14, pp. 150–152 (1989).

*Primary Examiner*—Richard L. Raymond
*Attorney, Agent, or Firm*—Marla J. Mathias; William A. Teoli, Jr.

[57] ABSTRACT

Compounds of the formula

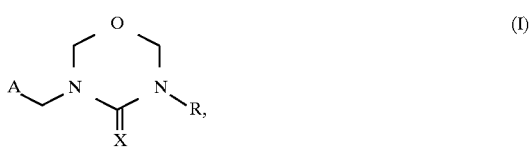

(I)

in which

A is an unsubstituted or mono- to tetrasubstituted, aromatic or non-aromatic, monocyclic or bicyclic heterocyclic radical, where one to two of the substituents of A can be selected from the group consisting of halo-$C_1$–$C_3$alkyl, cyclopropyl, halocyclopropyl, $C_2$–$C_3$alkenyl, $C_2$–$C_3$alkynyl, halo-$C_2$–$C_3$alkenyl, halo-$C_2$–$C_3$alkynyl, halo-$C_1$–$C_3$alkoxy, $C_1$–$C_3$alkylthio, halo-$C_1$–$C_3$alkylthio, allyloxy, propargyloxy, allylthio, propargylthio, haloallyloxy, haloallylthio, cyano and nitro, and one to four of the substituents of A can be selected from the group consisting of $C_1$–$C_3$alkyl, $C_1$–$C_3$alkoxy and halogen;

R is hydrogen, $C_1$–$C_6$alkyl, phenyl-$C_1$–$C_4$alkyl, $C_3$–$C_6$cycloalkyl, $C_2$–$C_6$alkenyl or $C_2$–$C_6$alkynyl; and X is N—$NO_2$ or N—CN, and, if appropriate, tautomers thereof, in each case in free form or in salt form, can be used as insecticidal active ingredients and can be prepared in a manner known per se.

10 Claims, No Drawings

OXADIAZINE DERIVATIVES

This is a divisional of Ser. No. 08/270,612, filed Jul. 5, 1994, now abandoned, which is a divisional of Ser. No. 08/091,801, filed Jul. 14, 1993, now abandoned.

The invention relates to compounds of the formula

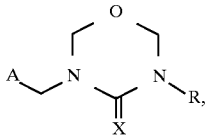

in which

A is an unsubstituted or mono- to tetrasubstituted, aromatic or non-aromatic, monocyclic or bicyclic heterocyclic radical, where one to two of the substituents of A can be selected from the group consisting of halo-$C_1$–$C_3$alkyl, cyclopropyl, halocyclopropyl, $C_2$–$C_3$alkenyl, $C_2$–$C_3$alkynyl, halo-$C_2$–$C_3$alkenyl, halo-$C_1$–$C_3$alkynyl, halo-$C_1$–$C_3$alkoxy, $C_1$–$C_3$alkylthio, halo-$C_1$–$C_3$alkylthio, allyloxy, propargyloxy, allylthio, propargylthio, haloallyloxy, haloallylthio, cyano and nitro, and one to four of the substituents of A can be selected from the group consisting of $C_1$–$C_3$alkyl, $C_1$–$C_3$alkoxy and halogen;

R is hydrogen, $C_1$–$C_6$alkyl, phenyl-$C_1$–$C_4$alkyl, $C_3$–$C_6$cycloalkyl, $C_2$–$C_6$alkenyl or $C_2$–$C_6$alkynyl; and X is N—$NO_2$ or N—CN, in free form or in salt form, and, if appropriate, to tautomers thereof, in free form or in salt form, to a process for the preparation and to the use of these compounds and tautomers, to pesticides whose active ingredient is selected from these compounds and tautomers, in each case in free form or in the form of agrochemically utilisable salts, to a process for the preparation and to the use of these compositions, to plant propagation material treated with these compositions, to a method of controlling pests, to intermediates, in free form or in salt form, for the preparation of these compounds, and, if appropriate, to tautomers, in free form or in salt form, thereof, and to a process for the preparation and to the use of these intermediates.

Certain oxadiazine derivatives have been proposed in the literature as arthropodacidally active active ingredients in pesticides. However, the biological properties of these known compounds are not always entirely satisfactory in the field of pest control, resulting in a demand for other compounds with pesticidal properties, in particular for controlling insects, this object being achieved according to the invention by providing the present compounds 1.

Some of the compounds I can exist in the form of tautomers. If, for example, R is hydrogen, then corresponding compounds I, i.e. those having a 3-H 4-imino-perhydro-1,3,5-oxadiazine part-structure, can exist in an equilibrium with the relevant tautomers, which have a 4amino-1,2,5,6-tetrahydro-1,3,5-oxadiazine part-structure. Accordingly, the compounds I hereinabove and hereinafter are, where appropriate, also to be understood as meaning corresponding tautomers, even when no specific mention is made of the latter in each individual case.

Compounds I which have at least one basic centre can form, for example, acid addition salts. These acid addition salts are formed, for example, with strong inorganic acids, such as mineral acids, for example perchloric acid, sulfuric acid, nitric acid, nitrous acid, a phosphoric acid or a hydrohalic acid, with strong organic carboxylic acids, such as unsubstituted or substituted, for example halogen-substituted, $C_1$–$C_4$alkanecarboxylic acids, for example acetic acid, or unsaturated or saturated dicarboxylic acids, for example oxalic acid, malonic acid, succinic acid, maleic acid, fumaric acid or phthalic acid, or hydroxycarboxylic acids, for example ascorbic acid, lactic acid, malic acid, tartaric acid or citric acid, or benzoic acid, or with organic sulfonic acids, such as unsubstituted or substituted, for example halogen-substituted, $C_1$–$C_4$alkane- or arylsulfonic acids, for example methane- or p-toluenesulfonic acid. Compounds I which have at least one acidic group can furthermore form salts with bases. Suitable salts with bases are, for example, metal salts such as alkali metal salts or alkaline earth metal salts, for example sodium salts, potassium salts or magnesium salts, or salts with ammonia or with an organic amine, such as morpholine, piperidine, pyrrolidine, a mono-, di- or tri-lower-alkylamine, for example ethyl-, diethyl-, triethyl- or dimethylpropylamine, or a mono-, di- or trihydroxy-lower-alkylamine, for example mono-, di- or triethanolamine. Moreover, corresponding internal salts may also be formed, where possible. Preferred salts within the scope of the invention are agrochemically advantageous salts; however, the invention also comprises salts which are disadvantageous for agrochemical purposes, for example salts which are toxic to honey bees or fish and which are employed, for example, for isolating or purifying free compounds I or agrochemically utilisable salts thereof. Due to the close relationship between the compounds I in free form and in the form of the salts thereof, the free compounds I, or the salts thereof, are to be understood analogously hereinabove and hereinafter as meaning, if appropriate, also the corresponding salts and the free compounds I, respectively. The same applies to tautomers of compounds I and salts thereof. Generally preferred is, in each case, the free form.

Unless otherwise defined, the general terms used hereinabove and hereinafter have the meanings given below.

Suitable hetero atoms in the basic ring structure of the heterocyclic radical A are all elements of the Periodic Table which can form at least two covalent bonds.

Halogen, as a group per se and as structural element of other groups and compounds, such as haloalkyl haloalkylthio, haloalkoxy, halocyclopropyl, haloalkenyl, haloalkynyl, haloallyloxy and haloallylthio, is fluorine, chlorine, bromine or iodine, in particular fluorine, chlorine or bromine, especially fluorine or chlorine, in particular chlorine.

Carbon-containing groups and compounds contain, unless otherwise defined, in each case 1 up to and including 6, preferably 1 up to and including 3, in particular 1 or 2, carbon atoms.

Cycloalkyl is cyclopropyl, cyclobutyl, cyclopentyl or cyclohexyl, preferably cyclopropyl.

Alkyl, as a group per se and as structural element of other groups and compounds, such as phenylalkyl, haloalkyl, alkoxy, haloalkoxy, alkylthio and haloalkylthio, is, in each case with due consideration of the number of carbon atoms contained in each case in the particular group or compound, either straight-chain, i.e. methyl, ethyl, propyl, butyl, pentyl or hexyl, or branched, for example isopropyl, isobutyl, sec-butyl, tert-butyl, isopentyl, neopentyl or isohexyl.

Alkenyl, haloalkenyl, alkynyl and haloalkynyl are straight-chain or branched and contain in each case two or, preferably, one unsaturated carbon-carbon bond(s). The double or triple bonds of these substituents are preferably separated from the remaining part of the compound I by at least one saturated carbon atom. Examples which may be mentioned are allyl, methallyl, but-2enyl, but-3-enyl, propargyl, but-2-ynyl and but-3-ynyl.

Halogen-substituted carbon-containing groups and compounds, such as haloalkyl, haloalkylthio, haloalkoxy, halocyclopropyl, haloalkenyl, haloalkynyl, haloallyloxy and haloallylthio, can be partially halogenated or perhalogenated, where, in the case of a polyhalogenation, the halogen sustituents can be identical or different. Examples of haloalkyl, as a group per se and as a structural element of other groups and compounds, such as haloalkylthio and haloalkoxy, are methyl which is mono- to trisubstituted by fluorine, chlorine and/or bromine, such as $CHF_2$ or $CF_3$; ethyl which is mono- to pentasubstituted by fluorine, chlorine and/or bromine, such as $CH_2CF_3$, $CF_2CF_3$, $CF_2CCl_3$, $CF_2CHCl_2$, $CF_2CHF_2$, $CF_2CFCl_2$, $CF_2CHBr_2$, $CF_2CHClF$, $CF_2CHBrF$ or $CClFCCHClF$; propyl or isopropyl, each of which is mono- to heptasubstituted by fluorine, chlorine and/or bromine, such as $CH_2CHBrCH_2Br$, $CF_2CHFCF_3$, $CH_2CF_2CF_3$, $CF_2CF_2CF_3$ or $CH(CF_3)_2$; and butyl or an isomer thereof, each of which can be mono- to nonasubstituted by fluorine, chlorine and/or bromine, such as $CF(CF_3)CHFCF_3$, $CF_2(CF_2)_2CF_3$ oder $CH_2(CF_2)_2CF_3$. Examples of haloalkenyl are 2,2-difluoroethen-1-yl, 2,2-dichloroethen-1-yl, 2-chloroprop-1-en-3-yl, 2,3-chloroprop-1-en-3-yl and 2,3-ibromoprop-1-en-3-yl. Examples of haloalkynyl are 2-chloroprop-1-yn-3-yl, 2,3-dichloroprop-1-yn-3-yl and 2,3-ibromoprop-1-yn-3-yl. Examples of halocyclopropyl are 2-chlorocyclopropyl, 2,2-difluorocyclopropyl and 2-chloro-2-fluorocyclopropyl. Examples of haloallyloxy are 2-chloroprop-1-en-3-yloxy, 2,3-dichloroprop-1-en-3-yloxy and 2,3-dibromoprop-1-en-3-yloxy. Examples of haloallylthio are 2-chloroprop-1-en-3-ylthio, 2,3-dichloroprop-1-en-3-ylthio and 2,3-dibromoprop-1-en-3-ylthio.

In phenylalkyl, an alkyl group bonded to the remainder of the compound I is substituted by a phenyl group, in this case the alkyl group preferably being straight-chained and the phenyl group preferably being bonded in a position higher than the α-position, most preferably in ω-position, of the alkyl group; examples are benzyl, 2-phenylethyl und 4-phenylbutyl.

Preferred embodiments within the scope of the invention are:

(1) a compound of the formula I in which
A is an unsubstituted or mono- to tetrasubstituted, aromatic or non-aromatic, monocyclic or bicyclic heterocyclic radical, where one to two of the substituents of A can be selected from the group consisting of halo-$C_1$–$C_3$alkyl, cyclopropyl, halocyclopropyl, $C_2$–$C_3$alkenyl, $C_2$–$C_3$alkynyl, halo-$C_2$–$C_3$alkenyl, halo-$C_2$–$C_3$alkynyl, halo-$C_1$–$C_3$alkoxy, $C_1$–$C_3$alkylthio, halo-$C_1$–$C_3$alkylthio, allyloxy, propargyloxy, allylthio, propargylthio, haloallyloxy, haloallylthio, cyano and nitro, and one to four of the substituents of A can be selected from the group consisting of $C_1$–$C_3$alkyl, $C_1$–$C_3$alkoxy and halogen;
R is hydrogen, $C_1$–$C_6$alkyl, $C_3$–$C_6$cycloalkyl, $C_2$–$C_6$alkenyl or $C_2$–$C_6$alkynyl; and
X is $N$—$NO_2$ or $N$—$CN$;

(2) a compound of the formula I in which the basic ring structure of A is composed of a ring which has 5 or 6 ring members and to which a further ring having 5 or 6 ring members can be fused,
in particular of a ring having 5 or, preferably, 6 ring members;

(3) a compound of the formula I in which the basic ring structure of A is unsaturated and has, in particular, one double bond or, preferably, 2 to 4, preferably conjugated, double bonds,
preferably in which the basic ring structure has 2, preferably conjugated, double bonds, in particular in which the basic ring structure has aromatic character;

(4) a compound of the formula I in which the basic ring structure of A has 1 up to and including 4, in particular 1 up to and including 3, especially 1 or 2, hetero atoms, particularly preferably 1 hetero atom;

(5) a compound of the formula I in which the basic ring structure of A is selected from the group consisting of the basic ring structures

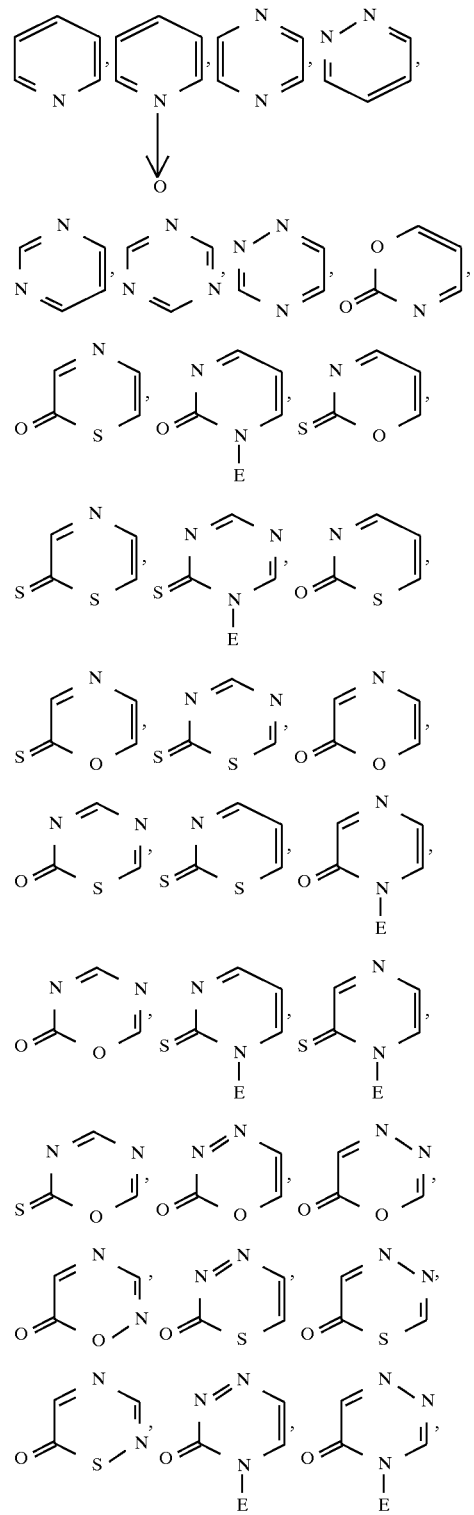

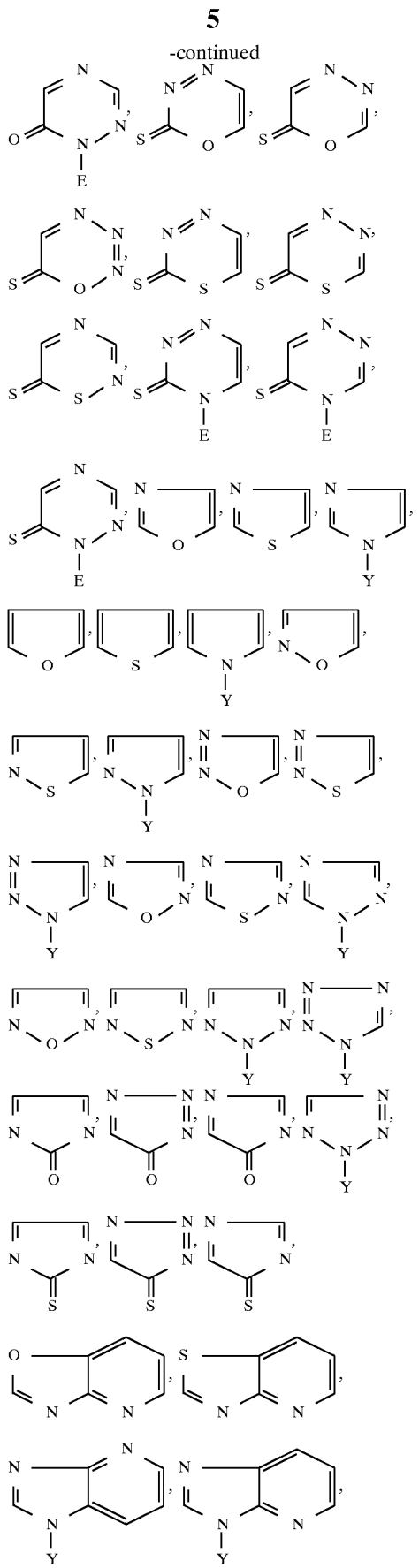

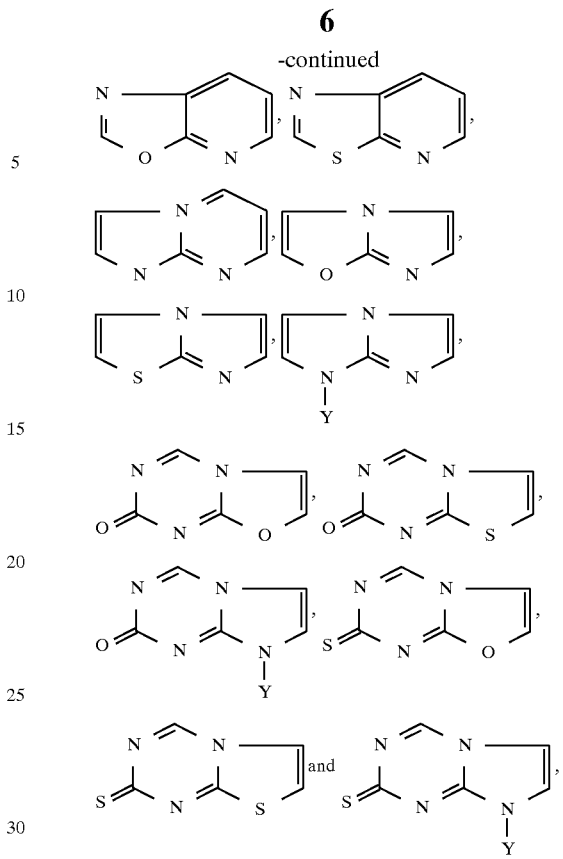

in which E is in each case $C_1$–$C_3$alkyl, Y is in each case hydrogen, $C_1$–$C_3$alkyl or cyclopropyl, and E and Y, respectively, are not regarded as a substituent of A but considered as part of the basic ring structure of A;

(6) a compound of the formula I in which the basic ring structure of A has 1, 2 or 3 hetero atoms selected from the group consisting of oxygen, sulfur and nitrogen, where not more than one of the hetero atoms in the basic ring structure is an oxygen atom and not more than one of the hetero atoms in the basic ring structure is a sulfur atom, in particular in which the basic ring structure has 1, 2 or 3 hetero atoms selected from the group consisting of oxygen, sulfur and nitrogen, where not more than one of the hetero atoms in the basic ring structure is an oxygen or a sulfur atom, preferably at least one nitrogen atom;

(7) a compound of the formula I, in which A is bonded via a C atom of its basic ring structure to the remaining part of the compound I;

(8) a compound of the formula I in which A is unsubstituted or mono- or disubstituted by substituents selected from the group consisting of halogen, $C_1$–$C_3$alkyl, halo-$C_1$–$C_3$alkyl, $C_1$–$C_3$alkoxy and halo-$C_1$–$C_3$-alkoxy, preferably in which A is unsubstituted or mono- or disubstituted by substituents selected from the group consisting of halogen and $C_1$–$C_3$alkyl;

(9) a compound of the formula I in which the basic ring structure of A is a pyridyl, 1-oxidopyridinio or thiazolyl group,
preferably in which the basic ring structure of A is a pyrid-3-yl, 1-oxido-3-pyridinio or thiazol-5-yl group,
in particular in which A is a pyrid-3-yl, 2-halopyrid-5-yl-, 2,3-dihalopyrid-5-yl, 2-$C_1$–$C_3$alkylpyrid-5-yl, 1-oxido-3-pyridinio, 2-halo-1-oxido-5-pyridinio, 2,3-dihalo-1-oxido-5-pyridinio or 2-halothiazol-5-yl group,
in particular in which A is a pyrid-3-yl, 2-halopyrid-5-yl, 2-halo-1-oxido-5-pyridinio or 2-halothiazol-5-yl group, preferably in which A is a 2-chloropyrid-5-yl, 2-methylpyrid-5-yl, 1-oxido-3-pyridinio, 2-chloro-1-oxido-5-pyridinio, 2,3-dichloro-1-oxido-5-pyridinio or 2-chlorothiazol-5-yl group, especially in which A is a pyrid-3-yl, 2-chloropyrid-5-yl, 2-chlor-1-oxido-5-pyridinio or 2-chlorothiazol-5-yl group, in particular in which A is a 2-chloropyrid-5-yl or, preferably, a 2-chlorothiazol-5-yl group;

(10) a compound of the formula I in which R is $C_1$–$C_6$alkyl, phenyl-$C_1$–$C_4$alkyl, $C_3$–$C_6$cycloalkyl, $C_3$–$C_4$alkenyl or $C_3$–$C_4$alkynyl, preferably $C_1$–$C_6$alkyl, $C_3$–$C_6$cycloalkyl, $C_3$–$C_4$alkenyl or $C_3$–$C_4$alkynyl, especially $C_1$–$C_6$alkyl, phenyl-$C_1$–$C_4$alkyl, $C_3$–$C_4$alkenyl or $C_3$–$C_4$alkynyl, in particular $C_1$–$C_4$alkyl, preferably methyl;

(11) a compound of the formula I in which X is N—$NO_2$;

(12) a compound of the formula I in which A is a pyridyl, 1-oxidopyridinio or thiazolyl group which is bonded via a C atom of its basic ring structure to the remaining part of the compound I and which is unsubstituted or mono- or disubstituted by substituents selected from the group consisting of halogen and $C_1$–$C_3$alkyl, R is $C_1$–$C_6$alkyl, phenyl-$C_1$–$C_4$alkyl, $C_3$–$C_6$cycloalkyl, $C_3$–$C_4$alkenyl or $C_3$–$C_4$alkynyl and X is N—$NO_2$ or N—CN;

(13) a compound of the formula I in which A is a 2-chloropyrid-5-yl, 2-methylpyrid-5-yl, 1-oxido-3-pyridinio, 2-chloro-1-oxido-5-pyridinio, 2,3-dichloro-1-oxido-5-pyridinio or 2-chlorothiazol-5-yl group, R is $C_1$–$C_4$alkyl and X is N—$NO_2$;

(14) a compound of the formula I in which A is a 2-chlorothiazol-5-yl or 2-chloropyrid-5-yl group, R is $C_1$–$C_4$alkyl and X is N—$NO_2$.

Compounds of the formula I which are particularly preferred within the scope of the invention are those mentioned in Examples H3 and H4.

Specifically preferred compounds within the scope of the invention are (a) 5-(2-chloropyrid-5-ylmethyl)-3-methyl-4-nitroiminoperhydro-1,3,5-oxadiazine, (b) 5-(2-chlorothiazol-5-ylmethyl)-3-methyl-4-nitroiminoperhydro-1,3,5-oxadiazine, (c) 3-methyl-4-nitroimino-5-(1-oxido-3-pyridiniomethyl)perhydro-1,3,5-oxadiazine, (d) 5-(2-chloro-1-oxido-5-pyridiniomethyl)-3-methyl-4-nitroiminoperhydro-1,3,5-oxadiazine and (e) 3-methyl-5-(2-methylpyrid-5-ylmethyl)-4-nitroiminoperhydro-1,3,5-oxadiazine.

As another object of the invention, the process for the preparation of the compounds of the formula I or, if appropriate, the tautomers thereof, in each case in free form or in salt form, comprises, for example, a) reacting a compound of the formula

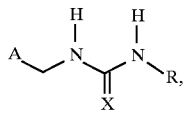 (II)

which is known or can be prepared in analogy to corresponding known compounds and in which A, R and X are as defined in formula I, or a tautomer and/or salt thereof, with formaldehyde or paraformaldehyde, preferably in the presence of a base or furthermore in the presence of an acid catalyst, or b) to prepare a compound of the formula I in which R is other than hydrogen, or, if appropriate, a tautomer and/or salt thereof, reacting, preferably in the presence of a base, a compound of the formula I in which R is hydrogen and which can be obtained, for example, according to variant a) or c), or a tautomer and/or salt thereof, with a compound of the formula

 (III), which is known or can be prepared in analogy to corresponding known compounds, and in which R is as defined in formula I with the exception of hydrogen and Y is a leaving group, or c) reacting, preferably in the presence of a base, a compound of the formula

 (IV)

in which R and X are as defined in formula I, or a tautomer and/or salt thereof, with a compound of the formula

 (V), which is known or can be prepared in analogy to corresponding known compounds, and in which A is as defined in formula I and Y is a leaving group, or, if appropriate, with a tautomer and/or salt thereof, and/or, if desired, converting a compound of the formula I or tautomer thereof, in each case in free form or in salt form, which can be obtained according to the process or by a different method, into a different compound of the formula I or a tautomer thereof, separating an isomer mixture which can be obtained according to the process, isolating the desired isomer, and/or converting a free compound of the formula I or a tautomer thereof, which can be obtained according to the process or by a different method, into a salt, or converting a salt of a compound of the formula I or of a tautomer thereof, which can be obtained according to the process or by a different method, into the free compound of the formula I or into a tautomer thereof, or into a different salt.

What has been said hereinabove for tautomers and/or salts of compounds I applies analogously to starting materials mentioned hereinabove and hereinafter with regard to the tautomers and/or salts thereof.

The reactions described hereinabove and hereinafter are carried out, for example, in the absence or, conventionally, in the presence of a suitable solvent or diluent or a mixture of these, the process being carried out, as required, with cooling, at room temperature or with heating, for example in a temperature range from approximately –80° C. to the boiling point of the reaction mixture, preferably from approximately –20° C. to approximately +150° C., and, if necessary, in a sealed container, under pressure, in an inert gas atmosphere and/or under anhydrous conditions. Particularly advantageous reaction conditions can be found in the Examples.

The starting materials mentioned hereinabove and hereinafter which are used for the preparation of the compounds I or, if appropriate, of the tautomers thereof, in each case in free form or in salt form, are known or can be prepared by methods known per se, for example by the information given hereinafter.

Variant a):

Suitable bases for facilitating the reaction are, for example, the hydroxides, hydrides, amides, alkanolates, acetates, carbonates, dialkylamides or alkylsilylamides of alkali metals or alkaline earth metals, alkylamines, alkylenediamines, free or N-alkylated, saturated or unsaturated cycloalkylamines, basic heterocycles, ammonium hydroxides and carbocyclic amines. Examples which may be mentioned are sodium hydroxide, sodium hydride, sodium amide, sodium methanolate, sodium acetate, sodium carbonate, potassium tert-butanolate, potassium hydroxide, potassium carbonate, potassium hydride, lithium diisopropylamide, potassium bis(trimethylsilyl)amide, calcium hydride, triethylamine, diisopropylethylamine, triethylenediamine, cyclohexylamine, N-cyclohexyl-N,N-dimethylamine, N,N-diethylaniline, pyridine, 4-(N,N-dimethylamino)-pyridine, quinuclidine, N-methylmorpholine, benzyltrimethylammoniumhydroxide and 1,5-diazabicyclo[5.4.0]undec-5-ene (DBU).

Suitable acid catalysts for facilitating the reaction are, for example, those acids, employed in catalytic amounts, which have been mentioned hereinabove as being suitable for the formation of acid addition salts with compounds I.

The reactants can be reacted with each other as such, i.e. without adding a solvent or diluent, for example in the molten state. However, in most cases it is advantageous to add an inert solvent or diluent or a mixture of these. The following may be mentioned as examples of such solvents or diluents: aromatic, aliphatic and alicyclic hydrocarbons and halohydrocarbons, such as benzene, toluene, xylene, mesitylene, tetralin, chlorobenzene, dichlorobenzene, bromobenzene, petroleum ether, hexane, cyclohexane, dichloromethane, trichloromethane, tetrachloromethane, dichloroethane, trichloroethene or tetrachloroethene; esters, such as ethyl acetate; ethers, such as diethyl ether, dipropyl ether, diisopropyl ether, dibutyl ether, tert-butyl methyl ether, ethylene glycol monomethyl ether, ethylene glycol monoethyl ether, ethylene glycol dimethyl ether, dimethoxydiethyl ether, tetrahydrofuran or dioxane; ketones, such as acetone, methyl ethyl ketone or methyl isobutyl ketone; alcohols, such as methanol, ethanol, propanol, isopropanol, butanol, ethylene glycol or glycerol; amides, such as N,N-dimethylformamide, N,N-diethylformamide, N,N-dimethylacetamide, N-methylpyrrolidone or hexamethylphosphoric triamide; nitriles, such as acetonitrile or propionitrile; and sulfoxides, such as dimethyl sulfoxide. If the reaction is carried out in the presence of a base, then bases which are employed in excess, such as triethylamine, pyridine, N-methylmorpholine or N,N-diethylaniline, can also act as solvents or diluents. If the reaction is carried out in the presence of an acid catalyst, then acids which are employed in excess, for example strong organic carboxylic acids, such as unsubstituted or substituted, for example halogen-substituted, $C_1$–$C_4$alkanecarboxylic acids, for example formic acid, acetic acid or propionic acid, can also act as solvents or diluents.

The reaction is advantageously carried out in a temperature range from approximately 0° C. to approximately +180° C., preferably from approximately +10° C. to approximately +130° C., in many cases in the range between room temperature and the reflux temperature of the reaction mixture.

If desired, the water of reaction, which is formed during the reaction, can be removed with the aid of a water separator, by azeotropic distillation or by adding a suitable molecular sieve.

Variant b):

Suitable leaving groups Y in the compounds m are, for example, hydroxyl, $C_1$–$C_8$alkoxy, halo-$C_1$–$C_8$alkoxy, $C_1$–$C_8$alkanoyloxy, mercapto, $C_1$–$C_8$alkylthio, halo-$C_1$–$C_8$alkylthio, $C_1$–$C_8$alkanesulfonyloxy, halo-$C_1$–$C_8$alkanesulfonyloxy, benzenesulfonyloxy, toluenesulfonyloxy and halogen.

Suitable bases for facilitating the detachment of HY are, for example, of the type given in variant a).

The reactants can be reacted with each other as such, i.e. without adding a solvent or diluent, for example in the molten state. However, in most cases it is advantageous to add an inert solvent or diluent or a mixture of these. The following may be mentioned as examples of such solvents or diluents: aromatic, aliphatic and alicyclic hydrocarbons and halohydrocarbons, such as benzene, toluene, xylene, mesitylene, tetralin, chlorobenzene, dichlorobenzene, bromobenzene, petroleum ether, hexane, cyclohexane, dichloromethane, trichloromethane, tetrachloromethane, dichloroethane, trichloroethene or tetrachloroethene; esters, such as ethyl acetate; ethers, such as diethyl ether, dipropyl ether, diisopropyl ether, dibutyl ether, tert-butyl methyl ether, ethylene glycol monomethyl ether, ethylene glycol monoethyl ether, ethylene glycol dimethyl ether, dimethoxydiethyl ether, tetrahydrofuran or dioxane; ketones, such as acetone, methyl ethyl ketone or methyl isobutyl ketone; alcohols, such as methanol, ethanol, propanol, isopropanol, butanol, ethylene glycol or glycerol; amides, such as N,N-dimethylformamide, N,N-diethylformamide, N,N-dimethylacetamide, N-methylpyrrolidone or hexamethylphosphoric triamide; nitriles, such as acetonitrile or propionitrile; and sulfoxides, such as dimethyl sulfoxide. If the reaction is carried out in the presence of a base, then bases which are employed in excess, such as triethylamine, pyridine, N-methylmorpholine or N,N-diethylaniline, can also act as solvents or diluents.

The reaction is advantageously carried out in a temperature range from approximately 0° C. to approximately +180° C., preferably from approximately +10° C. to approximately +130° C., in many cases in the range between room temperature and the reflux temperature of the reaction mixture.

Variant c):

Suitable leaving groups Y in the compounds V are, for example, of the type given in variant b).

Suitable bases for facilitating the detachment of HY are, for example, of the type given in variant a).

The reactants can be reacted with each other as such, i.e. without adding a solvent or diluent, for example in the molten state. However, in most cases it is advantageous to add an inert solvent or diluent or a mixture of these. Suitable solvents or diluents are, for example, of the type given under variant b).

The reaction is advantageously carried out in a temperature range from approximately −20° C. to approximately +180° C., preferably from approximately +10° C. to approximately +100° C., in many cases in the range between room temperature and the reflux temperature of the reaction mixture.

The compounds IV and the tautomers thereof, in each case in free form or in salt form, which are employed as educts in process variant c) are novel and also form part of the invention. Particularly preferred compounds within the scope of the invention are the compounds of the formula IV mentioned in Examples H1 and H2 and the tautomers thereof.

The invention also relates to the process for the preparation of the compounds of the formula IV or the tautomers thereof, in each case in free form or in salt form, which comprises, for example, d) reacting a compound of the formula

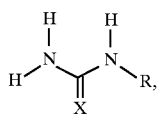 (VI)

which is known or can be prepared in analogy to corresponding known compounds, and in which R and X are as defined in formula I, or a tautomer and/or salt thereof, with formaldehyde or paraformaldehyde, for example analogously to the manner described under variant a) for the corresponding reaction of a compound of the formula II or of a tautomer and/or salt thereof with formaldehyde or paraformaldehyde, or e) to prepare a compound of the formula IV in which R is other than hydrogen, or of a tautomer and/or salt thereof, reacting a compound of the formula IV which can be obtained, for example, according to variant d) and in which R is hydrogen, or a tautomer and/or salt thereof, with a compound of the formula

 (III), which is known or can be prepared in analogy to corresponding known compounds and in which R is as defined in formula I with the exception of hydrogen and Y is a leaving group, for example analogously to the manner described under variant b) for the corresponding reaction of a compound of the formula I or, if appropriate, a tautomer and/or salt thereof, with a compound of the formula III, and/or, if desired, converting a compound of the formula IV or a tautomer thereof, in each case in free form or in salt form, which can be obtained according to the process or by a different method, into a different compound of the formula IV or a tautomer thereof, separating an isomer mixture which can be obtained according to the process, isolating the desired isomer, and/or converting a free compound of the formula IV or a tautomer thereof, which can be obtained according to the process or by a different method, into a salt, or converting a salt of a compound of the formula IV or of a tautomer thereof, which can be obtained according to the process or by a different method, into the free compound of the formula IV or into a tautomer thereof, or into a different salt.

A compound I or IV which can be obtained according to the process or by a different method can be converted into a different compound I or IV in a manner known per se by replacing one or more substituents of the starting compound I or IV by (a) different substituent(s) according to the invention.

In the case of compounds I which have an unsubstituted radical A, for example, substituents can be introduced into the radical A, or, in the case of compounds I which have a substituted radical A, for example, substituents of the radical A can be replaced by other substituents.

Depending on which reaction conditions and stating materials are selected as being suitable for this purpose, it is possible to replace, in one reaction step, only one substituent by a different substituent according to the invention, or several substituents can be replaced in the same reaction step by other substituents according to the invention.

Salts of compounds I or IV can be prepared in a manner known per se. For example, acid addition salts of compounds I or IV are obtained by treating them with a suitable acid or a suitable ion-exchanger reagent, and salts with bases are obtained by treating them with a suitable base or a suitable ion-exchanger reagent Salts of compounds I or IV can be converted in the customary manner into the free compounds I or IV, for example acid addition salts by being treated with a suitable basic agent or a suitable ion-exchanger reagent, and salts with bases, for example, by being treated with a suitable acid or a suitable ion-exchanger reagent.

Salts of compounds I or IV can be converted in a manner known per se into different salts of compounds I or IV, for example acid addition salts into different acid addition salts, for example by treating a salt of an inorganic acid, such as a hydrochloride, with a suitable metal salt, such as a sodium salt, barium salt or silver salt, of an acid, for example using silver acetate, in a suitable solvent, in which an inorganic salt which is being formed, for example silver chloride, is insoluble and so separates out from the reaction mixture.

Depending on the procedure and the reaction conditions, the compounds I and IV which have salt-forming properties can be obtained in free form or in the form of salts.

The compounds I and IV and in each case, if appropriate, the tautomers thereof, in each case in free form or in salt form, can be present in the form of one of the isomers which are possible or as a mixture of these, for example as pure isomers, such as antipodes and/or diastereomers, or as isomer mixtures, such as enantiomer mixtures, for example racemates, diastereomer mixtures or racemate mixtures, depending on the number and the absolute and relative configuration of asymmetric carbon atoms in the molecule and/or depending on the configuration of non-aromatic double bonds in the molecule; the invention relates to the pure isomers and to all isomer mixtures which are possible and is to be understood accordingly in each case hereinabove and hereinafter, even when stereochemical details are not mentioned specifically in each individual case.

Diastereomer mixtures and racemate mixtures of compounds I or IV, in free form or in salt form, which can be obtained according to the process—depending on which starting materials and procedures are selected—or by other routes, can be separated on the basis of the physicochemical differences of the components in the known manner to give the pure diastereomers or racemates, for example by fractional crystallisation, distillation and/or chromatography.

Enantiomer mixtures which can be obtained accordingly, such as racemates, can be resolved by known methods to give the optical antipodes, for example by recrystallisation from an optically active solvent, by chromatography on chiral adsorbents, for example high-pressure liquid chromatography (HPLC) on acetylcellulose, with the aid of suitable microorganisms, by cleavage using specific, immobilised enzymes, via the formation of inclusion compounds, for example using chiral crown ethers, where only one enantiomer is complexed, or by conversion into diastereomeric salts, for example by reacting a basic end-product racemate with an optically active acid, such as a carboxylic acid, for example camphoric acid, tartaric acid or malic acid, or a sulfonic acid, for example camphorsulfonic acid, and separating the resulting mixture of diastereomers, for example by fractional crystallisation since they differ with regard to their solubility properties, to give the diastereomers, from which the enantiomer desired can be liberated by allowing suitable agents, for example bases, to act on them.

Pure diastereomers or enantiomers can be obtained according to the invention not only by separating suitable isomer mixtures but also by generally known methods of diastereoselective or enantioselective synthesis, for example by carrying out the process according to the invention using stereochemically suitable educts.

If the individual components differ with regard to their biological activity, it is advantageous to isolate, or synthesise, in each case the biologically more effective isomer, for example enantiomer or diastereomer, or isomer mixture, for example enantiomer mixture or diastereomer mixture.

The compounds I and IV, in free form or in salt form, can also be obtained in the form of their hydrates and/or can also include other solvents, for example solvents which may be used for crystallising compounds in solid form.

The invention relates to all those embodiments of the process in which, starting from a starting material or intermediate which can be obtained in any desired step of the process, all or some of the missing steps are carried out or a starting material is used in the form of a derivative or salt thereof and/or the racemates or antipodes thereof or, in particular, formed under the reaction conditions.

Starting materials and intermediates, in each case in free form or in salt form, which are used in the process of the present invention are preferably those which lead to the compounds I which have been described at the outset as being particularly valuable, or to salts thereof.

The invention particularly relates to the preparation processes described in Examples H1 to H4.

The invention furthermore relates to starting materials and intermediates, in each case in free form or in salt form, which are novel and which are used according to the invention for the preparation of the compounds I or salts thereof, to a process for their preparation and to their use as starting materials and intermediates for the preparation of the compounds I; in particular, this applies to the compounds IV.

The compounds I according to the invention are active ingredients in the field of pesticides which have a very favourable biocidal spectrum and are valuable when used preventively and/or curatively even at low rates of application, while being well tolerated by warm-blooded species, fish and plants. The active ingredients according to the invention are effective against all or individual development stages of normally sensitive, but also resistant, animal pests, such as insects. The insecticidal action of the active ingredients according to the invention can become apparent either directly, i.e. by destroying the pests, either immediately or only after some time has elapsed, for example during moulting, or indirectly, for example by a reduced oviposition and/or hatching rate where the good activity corresponds to a mortality rate of at least 50 to 60%.

Examples of the abovementioned animal pests are:
from the order Lepidoptera, for example, Acleris spp., Adoxophyes spp., Aegeria spp., Agrotis spp., *Alabama argillaceae,* Amylois spp., *Anticarsia gemmatalis,* Archips spp., Argyrotaenia spp., Autographa spp., *Busseola fusca, Cadra cautella, Carposina nipponensis,* Chilo spp., Choristoneura spp., *Clysia ambiguella,* Cnaphalocrocis spp., Cnephasia spp., Cochylis spp., Coleophora spp., *Crocidolomia binotalis, Cryptophlebia leucotreta,* Cydia spp., Diatraea spp., *Diparopsis castanea,* Earias spp., Ephestia spp., *Eupoecilia ambiguella,* Euproctis spp., Euxoa spp., Grapholita spp., *Hedya nubiferana,* Heliothis spp., *Hellula undalis, Hyphantria cunea, Keiferia lycopersicella, Leucoptera scitella,* Lithocollethis spp., *Lobesia botrana,* Lymantria spp., Lyonetia spp., Malacosoma spp., *Mamestra brassicae, Manduca sexta,* Operophtera spp., *Ostrinia nubilalis,* Pammene spp., Pandemis spp., *Panolis flammea, Pectinophora gossypiella, Phthorimaea operculella, Pieris rapae,* Pieris spp., *Plutella xylostella,* Prays spp., Scirpophaga spp., Sesamia spp., Sparganothis spp., Spodoptera spp., Synanthedon spp., Thaumetopoea spp., Tortrix spp., *Trichoplusia ni* and Yponomeuta spp.;

from the order Coleoptera, for example,

Agriotes spp., Anthonomus spp., *Atomaria linearis, Chaetocnema tibialis,* Cosmopolites spp., Curculio spp., Dermestes spp., Diabrotica spp., Epilachna spp., Eremnus spp., *Leptinotarsa decemlineata,* Lissorhoptrus spp., Melolontha spp., Orycaephilus spp., Otiorhynchus spp., Phlyctinus spp., Popillia spp., Psylliodes spp., Rhizopertha spp., Scarabeidae, Sitophilus spp., Sitotroga spp., Tenebrio spp., Tribolium spp. and Trogoderma spp.;

from the order Orthoptera, for example,

Blatta spp., Blattella spp., Gryllotalpa spp., *Leucophaea maderae,* Locusta spp., Periplaneta spp. and Schistocerca spp.;

from the order Isoptera, for example,

Reticulitermes spp.;

from the order Psocoptera, for example,

Liposcelis spp.;

from the order Anoplura, for example,

Haematopinus spp., Linognathus spp., Pediculus spp., Pemphigus spp. and Phylloxera spp.;

from the order Mallophaga, for example,

Damalinea spp. and Trichodectes spp.;

from the order Thysanoptera, for example,

Franklinella spp., Hercinothrips spp., Taeniothrips spp., *Thrips palmi, Thrips tabaci* and *Scirtothrips aurantii;* from the order Heteroptera, for example,

Cimex spp., *Distantiella theobroma,* Dysdercus spp., Euchistus spp., Eurygaster spp., Leptocorisa spp., Nezara spp., Piesma spp., Rhodnius spp., *Sahlbergella singularis,* Scotinophara spp. and Triatoma spp.;

from the order Homoptera, for example,

*Aleurothrixus floccosus, Aleyrodes brassicae,* Aonidiella spp., Aphididae, Aphis spp., Aspidiotus spp., *Bemisia tabaci,* Ceroplaster spp., *Chrysomphalus aonidium, Chrysomphalus dictyospermi, Coccus hesperidum,* Empoasca spp., *Eriosoma larigerum,* Erythroneura spp., Gascardia spp., Laodelphax spp., *Lecanium corni,* Lepidosaphes spp., Macrosiphus spp., Myzus spp., Nephotettix spp., Nilaparvata spp., Paratoria spp., Pemphigus spp., Planococcus spp., Pseudaulacaspis spp., Pseudococcus spp., Psylla spp., *Pulvinaria aethiopica,* Quadraspidiotus spp., Rhopalosiphum spp., Saissetia spp., Scaphoideus spp., Schizaphis spp., Sitobion spp., *Trialeurodes vaporariorum, Trioza erytreae* and *Unaspis citri;* from the order Hymenoptera, for example,

Acromyrmex, Atta spp., Cephus spp., Diprion spp., Diprionidae, *Gilpinia polytoma,* Hoplocampa spp., Lasius spp., *Monomorium pharaonis,* Neodiprion spp., Solenopsis spp. and Vespa spp.;

from the order Diptera, for example,

Aedes spp., *Antherigona soccata, Bibio hortulanus, Calliphora erythrocephala,* Ceratitis spp., Chrysomyia spp., Culex spp., Cuterebra spp., Dacus spp., *Drosophila melanogaster,* Fannia spp., Gastrophilus spp., Glossina spp., Hypoderma spp., Hyppobosca spp., Liriomyza spp., Lucilia spp., Melanagromyza spp., Musca spp., Oestrus spp., Orseolia spp., *Oscinella frit, Pegomyia hyoscyami,* Phorbia spp., *Rhagoletis pomonella,* Sciara spp., Stomoxys spp., Tabanus spp., Tannia spp. and Tipula spp.;

from the order Siphonaptera, for example,

Ceratophyllus spp. und *Xenopsylla cheopis* and from the order Thysanura, for example,

*Lepisma saccharina.*

The active ingredients according to the invention allow pests of the abovementioned type to be controlled, i.e. contained or destroyed, which occur in particular on plants, especially on useful plants and ornamentals in agriculture, horticulture and forests, or on parts of such plants, such as fruits, flowers, foliage, stalks, tubers or roots, and, in some cases, even newly-forming parts of the plants are still protected against these pests.

Suitable as target crops are, in particular, cereals, such as wheat, barley, rye, oats, rice, maize or sorghum; beets, such as sugar beet or fodder beet; fruit, for example pome fruit, stone fruit and soft fruit, such as apples, pears, plums, peaches, almonds, cherries, or berries, for example strawberries, raspberries or blackberries; leguminous plants, such as beans, lentils, peas or soya beans; oil crops, such as oilseed rape, mustard, poppies, olives, sunflowers, coconut, castor, cocoa, or groundnuts; cucurbits, such as pumpkins, cucumbers or melons; fibre plants, such as cotton, flax, hemp or jute; citrus fruits, such as oranges, lemons, grapefruit or tangerines; vegetables, such as spinach, lettuce, asparagus, cabbages, carrots, onions, tomatoes, potatoes or bell peppers; Lauraceae, such as avocado, cinnamon or camphor, and also tobacco, nuts, coffee, egg plants, sugar cane, tea, pepper, vines, hops, Musaceae, latex plants and ornamentals.

The active ingredients according to the invention are particularly suitable for controlling *Aphis craccivora, Bemisia tabaci, Diabrotica balteata, Heliothis virescens, Myzus persicae, Nephotettix cincticeps* and *Nilaparvata lugens* in vegetable, maize, fruit, rice and soya bean crops.

Other fields of application for the active ingredients according to the invention are the protection of stored products and stores and of material and, in the hygiene sector, in particular the protection of domestic animals and productive livestock against pests of the abovementioned type.

The invention therefore also relates to pesticides, such as emulsifiable concentrates, suspension concentrates, directly sprayable or dilutable solutions, spreadable pastes, dilute emulsions, wettable powders, soluble powders, dispersible powders, dusts, granules or encapsulations in polymeric substances, all of which comprise at least one of the active ingredients according to the invention and are to be selected depending on the intended aims and the prevailing circumstances.

In these compositions, the active ingredient is used as a pure active ingredient, for example a solid active ingredient in a specific particle size or, preferably, together with at least one of the auxiliaries conventionally used in the art of formulation, such as extenders, for example solvents or solid carriers, or such as surface-active compounds (surfactants).

Examples of suitable solvents are: unhydrogenated or partially hydrogenated aromatic hydrocarbons, preferably the fractions $C_8$ to $C_{12}$ of alkylbenzenes, such as xylene mixtures, alkylated naphthalenes or tetrahydronaphthalene, aliphatic or cycloaliphatic hydrocarbons, such as paraffins or cyclohexane, alcohols, such as ethanol, propanol or butanol, glycols and the ethers and esters thereof, such as propylene glycol, dipropylene glycol ether, ethylene glycol or ethylene glycol monomethyl ether or ethylene glycol monoethyl ether, ketones, such as cyclohexanone, isophorone or diacetanol alcohol, strongly polar solvents, such as N-methylpyrrolid-2-one, dimethyl sulfoxide or N,N-dimethylformamide, water, epoxidised or unepoxidised vegetable oils, such as epoxidised or unepoxidised rapeseed oil, castor oil, coconut oil or soya oil, and silicone oils.

Solid carriers which are used, for example for dusts and dispersible powders, are, as a rule, ground natural minerals, such as calcite, talc, kaolin, montmorillonite or attapulgite. To improve the physical properties, it is also possible to add highly-disperse silicas or highly-disperse absorptive polymers. Possible particulate, adsorptive carriers for granules are either porous types, such as pumice, brick grit, sepiolite or bentonite, or non-sorptive carrier materials, such as calcite or sand. In addition, a large number of granulated materials of inorganic or organic nature can be used, in particular dolomite or comminuted plant residues.

Depending on the nature of the active ingredient to be formulated, suitable surface-active compounds are nonionic, cationic and/or anionic surfactants or surfactant mixtures which have good emulsifying, dispersing and wetting properties. The surfactants given hereinbelow are only to be regarded as examples; the specialist literature describes a large number of further surfactants conventionally used in the art of formulation and suitable according to the invention.

Suitable non-ionic surfactants are mainly polyglycol ether derivatives of aliphatic or cycloaliphatic alcohols, saturated or unsaturated fatty acids and alkylphenols which can have 3 to 30 glycol ether groups and 8 to 20 carbon atoms in the (aliphatic) hydrocarbon radical and 6 to 18 carbon atoms in the alkyl radical of the alkylphenols. Other suitable substances are water-soluble polyethylene oxide adducts with polypropylene glycol, ethylenediaminopolypropylene glycol and alkylpolypropylene glycol having 1 to 10 carbon atoms in the alkyl chain and 20 to 250 ethylene glycol ether groups and 10 to 100 propylene glycol ether groups. Conventionally, the abovementioned compounds contain 1 to 5 ethylene glycol units per propylene glycol unit. Examples which may be mentioned are nonylphenol polyethoxyethanols, castor oil polyglycol ethers, polypropylene/polyethylene oxide adducts, tributylphenoxypolyethoxyethanol, polyethylene glycol and octylphenoxypolyethoxyethanol. Fatty acid esters of polyoxyethylene sorbitan, such as polyoxyethylene sorbitan trioleate, are furthermore suitable.

The cationic surfactants are mainly quaternary ammonium salts which have at least one alkyl radical having 8 to 22 C atoms as substituent and, as further substituents, lower, free or halogenated, alkyl, benzyl or lower hydroxyalkyl radicals. The salts are preferably in the form of halides, methylsulfates or ethylsulfates. Examples are stearyltrimethylammonium chloride and benzyl-di(2-chloroethyl) ethylammonium bromide.

Suitable anionic surfactants can be either water-soluble soaps or water-soluble synthetic surface-active compounds. Soaps which are suitable are the alkali metal salts, alkaline earth metal salts and unsubstituted or substituted ammonium salts of higher fatty acids ($C_{10}$–$C_{22}$), such as the sodium salts or potassium salts of oleic or stearic acid, or of natural mixtures of fatty acids which can be obtained, for example, from coconut oil or tall oil; mention must also be made of the fatty acid methyltaurinates. However, synthetic surfactants are used more frequently, in particular fatty sulfonates, fatty sulfates, sulfonated benzimidazole derivatives or alkylarylsulfonates. The fatty sulfonates and fatty sulfates are, as a rule, in the form of alkali metal salts, alkaline earth metal salts or substituted or unsubstituted ammonium salts and have, as a rule, an alkyl radical having 8 to 22 C atoms, alkyl also including the alkyl moiety of acyl radicals; examples which may be mentioned are the sodium salt or potassium salt of ligninsulfonic acid, of the dodecylsulfuric ester or of a fatty alcohol sulfate mixture prepared from natural fatty acids. This group also includes the salts of the sulfuric esters and sulfonic acids of fatty alcohol/ethylene oxide adducts. The sulfonated benzimidazole derivatives preferably have two sulfonyl groups and one fatty acid radical having approximately 8 to 22 C atoms. Examples of alkylarylsulfonates are the sodium salts, calcium salts or triethanolammonium salts of dodecylbenzenesulfonic acid, of dibutylnaphthalenesulfonic acid or of a naphthalenesulfonic acid/formaldehyde condensation product. Other substances which are possible are suitable phosphates, such as salts of the phosphoric ester of a p-nonylphenol/(4–14) ethylene oxide adduct, or phospholipids.

As a rule, the compositions comprise 0.1 to 99%, in particular 0.1 to 95%, of active ingredient and 1 to 99.9%, in particular 5 to 99.9%, of at least one solid or liquid auxiliary, where, as a rule, 0 to 25%, in particular 0.1 to 20%, of the compositions can be surfactants (% in each case meaning percent by weight). While concentrated compositions are more preferred as commercially available goods, the end consumer uses, as a rule, dilute compositions whose concentrations of active ingredient are considerably lower. Preferred compositions are, in particular, composed as follows (%=percent by weight):

Emulsifiable Concentrates:
Active ingredient: 1 to 90%, preferably 5 to 20%
Surfactant: 1 to 30%, preferably 10 to 20%
Solvent: 5 to 98%, preferably 70 to 85%
Dusts:
Active ingredient: 0.1 to 10%, preferably 0.1 to 1%
Solid carrier: 99.9 to 90%, preferably 99.9 to 99%
Suspension Concentrates:
Active ingredient: 5 to 75%, preferably 10 to 50%
Water: 94 to 24%, preferably 88 to 30%
Surfactant: 1 to 40%, preferably 2 to 30%
Wettable Powders:
Active ingredient: 0.5 to 90%, preferably 1 to 80%
Surfactant: 0.5 to 20%, preferably 1 to 15%
Solid carrier: 5 to 99%, preferably 15 to 98%
Granules:
Active ingredient: 0.5 to 30%, preferably 3 to 15%
Solid carrier: 99.5 to 70%, preferably 97 to 85%

The activity of the compositions according to the invention can be broadened considerably and adapted to prevailing circumstances by addition of other insecticidal active ingredients. Possible active ingredients which are added are, for example, representatives from the following classes of active ingredients: organophosphorus compounds, nitrophenols and derivatives, formamidines, ureas, carbamates, pyrethroids, chlorinated hydrocarbons and *Bacillus thuringiensis* preparations. The compositions according to the invention can also comprise other solid or liquid auxiliaries, such as stabilisers, for example epoxidised or unepoxidised vegetable oils (for example epoxidised coconut oil, rapeseed oil or soya oil), antifoams, for example silicone oil, preservatives, viscosity regulators, binders and/or tackifiers, and also fertilisers or other active ingredients for achieving specific effects, for example acaricides, bactericides, fungicides, nematocides, molluscicides or selective herbicides.

The compositions according to the invention are prepared in a known manner, for example, in the absence of auxiliaries, by grinding, screening and/or compressing a solid active ingredient, or active ingredient mixture, for example to give a certain particle size, and, in the presence of at least one auxiliary, for example by intimately mixing and/or grinding the active ingredient, or active ingredient mixture, with the auxiliary(-ies). The invention also relates to these processes for the preparation of the compositions according to the invention and to the use of the compounds I for the preparation of these compositions.

The invention furthermore relates to the methods of application of the compositions, i.e. to the methods of controlling pests of the abovementioned type, such as spraying, atomising, dusting, brushing-on, seed-dressing, scattering or pouring, which are to be selected depending on the intended aims and prevailing circumstances, and to the use of the compositions for controlling pests of the abovementioned type. Characteristic rates of concentration are between 0.1 and 1000 ppm, preferably between 0.1 and 500 ppm, of active ingredient. The application rates per hectare are, as a rule, 1 to 2000 g of active ingredient per hectare, in particular 10 to 1000 g/ha, preferably 20 to 600 g/ha.

A preferred method of application in the field of crop protection is application to the foliage of the plants (foliar application) where frequency and rate of application will depend on the danger of infestation with the particular pest. However, the active ingredient can also reach the plants via the root system (systemic action), by drenching the locus of the plants with a liquid composition or by incorporating the active ingredient in solid form into the locus of the plants, for example into the soil, for example in the form of granules (soil application). In paddy rice, such granules can be metered to the flooded paddy field.

The compositions according to the invention are also suitable for protecting plant propagation material, for example seed, such as fruits, tubers or kernels, or plant cuttings, against animal pests. The propagation material can be treated with the composition before planting, for example seed can be dressed before sowing. Alternatively, the active ingredients according to the invention can be applied to the seed kernels (coating), either by soaking the kernels in a liquid composition or by coating them with a solid composition. Alternatively, the composition can be applied to the site of planting when the propagation material is planted, for example it can be applied to the seed furrow during sowing. The invention furthermore relates to these methods for treating plant propagation material and the plant propagation material thus treated.

The Examples which follow are not limiting, but only intended to illustrate the invention. Temperatures are given in degrees celsius.

Preparation Examples

Example H1

3-Methyl-4-nitroiminoperhydro-1,3,5-oxadiazine

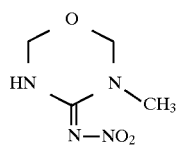

or 3-methyl-4-nitroamino-1,2,3,6-tetrahydro-1,3,5-oxadiazine, respectively

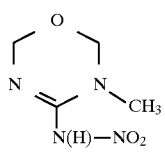

30.5 g of paraformaldehyde are added, at room temperature, to a mixture of 20 g of N-methyl-N'-nitroguanidine, 17 g of triethylamine, 100 ml of dioxane and 100 ml of toluene, and the mixture is refluxed for 16 hours and subsequently evaporated in vacuo. The residue is purified by column chromatography [silica gel; dichloromethane/methanol (95:5)], giving the title compound which melts at 137° to 139°.

Example H2

Analogously to the procedure described in Example H1 also the following compounds can be prepared:

3-ethyl-4-nitroimino-perhydro-1,3,5-oxadiazine or 3-ethyl-4-nitroamino-1,2,3,6-tetrahydro-1,3,5-oxadiazine, respectively, 4-nitroimino-3-propyl-perhydro-1,3,5-oxadiazine or 4nitroamino-3-propyl-1,2,3,6-tetrahydro-1,3,5-oxadiazine, respectively, (resin), 3-butyl-4-nitroimino-perhydro-1,3,5-oxadiazine or 3-butyl-4-nitroamino-1,2,3,6-tetrahydro-1,3,5-oxadiazine, respectively, (melting point: 80°–82°), 3-cyclopropyl-4-nitroimino-perhydro-1,3,5-oxadiazine or 3-cyclopropyl-4-nitroamino-1,2,3,6-tetrahydro-1,3,5-oxadiazine, respectively, 3-allyl-4-nitroimino-perhydro-1,3,5-oxadiazine or 3-allyl-4-nitroamino-1,2,3,6-tetrahydro-1,3,5-oxadiazine, respectively, (resin), 4-nitroimino-3-propargyl-perhydro-1,3,5-oxadiazine or 4-nitroamino-3-propargyl-1,2,3,6-tetrahydro-1,3,5-oxadiazine, respectively, (melting point: 102°–104°), 4-cyanoimino-3-methyl-perhydro-1,3,5-oxadiazine or 4-cyanoamino-3-methyl-1,2,3,6-tetrahydro-1,3,5-oxadiazine, respectively, (melting point: 121°–122°), 4-cyanoimino-3-ethyl-perhydro-1,3,5-oxadiazine or 4-cyanoamino-3-ethyl-1,2,3,6-tetrahydro-1,3,5-oxadiazine, respectively, 4-cyanoimino-3-cyclopropyl-perhydro-1,3,5-oxadiazine or 4cyanoamino-3-cyclopropyl-1,2,3,6-tetrahydro-1,3,5-oxadiazine, respectively, and 4nitroimino-3-(2-phenylethyl)-perhydro 1,3,5-oxadiazine or 4nitroamino-3-(2-phenylethyl)- 1,2,3,6-tetrahydro-1,3,5-oxadiazine, respectively, (melting point: 123°–125°).

Example H3

5-(2-Chloropyrid-5-ylmethyl)-3-methyl-4-nitroiminoperhydro-1,3,5-oxadiazine (Table 1, Compound No. 1.2).

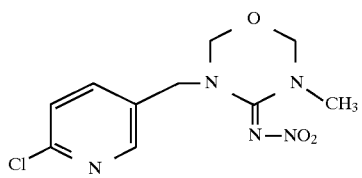

A mixture of 1.44 g of 3-methyl-4-nitroiminoperhydro-1,3,5-oxadiazine, 2.2 g of 2-chloro-5-chloromethylpyridine, 3.7 g of potassium carbonate and 20 ml of N,N-dimethylformamide is heated for 4 hours at 50° and filtered, the filtrate is evaporated in vacuo on a rotary evaporator, and the residue is purified by chromatography [silica gel; dichloromethane/methanol (95:5)]. This gives the title compound which melts at 116° to 118°.

Example H4

Analogously to the procedures described in Examples H1 to H3 also the other compounds listed in Tables 1 and 2 can be prepared. The temperatures given in the column "Physical Data" of these tables in each case denote the melting point of the compound in question.

TABLE 1

| Comp. No. | A | R | Physical Data |
|---|---|---|---|
| 1.1 | 3-pyridyl | CH$_3$ | |
| 1.2 | 2-chloro-5-pyridyl | CH$_3$ | 116–118° |
| 1.3 | 2-chloro-5-thiazolyl | CH$_3$ | 132–134° |
| 1.4 | 3-pyridyl N-oxide | CH$_3$ | 210° (decomposition) |
| 1.5 | 2-chloro-5-pyridyl N-oxide | CH$_3$ | 188–191° |
| 1.6 | 2,3-dichloro-5-pyridyl | CH$_3$ | |
| 1.7 | 2,3-dichloro-5-pyridyl N-oxide | CH$_3$ | 199° (decomposition) |
| 1.8 | 2-methyl-5-pyridyl | CH$_3$ | 141–144° |
| 1.9 | 2-chloro-5-pyridyl | C$_2$H$_5$ | |

TABLE 1-continued

Structure:

$$\text{A-CH}_2-\text{N}\underset{\underset{\text{N}-\text{NO}_2}{\parallel}}{\overset{\text{-CH}_2-\text{O}-\text{CH}_2\text{-}}{\frown}}\text{N}-\text{R}$$

| Comp. No. | A | R | Physical Data |
|---|---|---|---|
| 1.10 | 2-Cl-thiazol-5-yl | C₂H₅ | |
| 1.11 | 6-Cl-pyridin-3-yl | cyclopropyl | |
| 1.12 | 2-Cl-thiazol-5-yl | cyclopropyl | |
| 1.13 | 6-Cl-pyridin-3-yl | n-C₃H₇ | resin |
| 1.14 | 6-Cl-pyridin-3-yl | n-C₄H₉ | resin |
| 1.15 | 6-Cl-pyridin-3-yl | allyl | resin |
| 1.16 | 6-Cl-pyridin-3-yl | propargyl | 103–108° |
| 1.17 | 2-Cl-thiazol-5-yl | n-C₄H₉ | 71–73° |
| 1.18 | 2-Cl-thiazol-5-yl | propargyl | 176° |
| 1.19 | 6-Cl-pyridin-3-yl | CH₂CH₂—C₆H₅ | resin |
| 1.20 | 2-Cl-thiazol-5-yl | CH₂CH₂—C₆H₅ | resin |

TABLE 2

Structure:

$$\text{A-CH}_2-\text{N}\underset{\underset{\text{N}-\text{CN}}{\parallel}}{\overset{\text{-CH}_2-\text{O}-\text{CH}_2\text{-}}{\frown}}\text{N}-\text{R}$$

| Comp. No. | A | R | Physical Data |
|---|---|---|---|
| 2.1 | pyridin-3-yl | CH₃ | |
| 2.2 | 6-Cl-pyridin-3-yl | CH₃ | 108–109° |
| 2.3 | 2-Cl-thiazol-5-yl | CH₃ | 92–93° |
| 2.4 | pyridin-3-yl N-oxide | CH₃ | |
| 2.5 | 6-Cl-pyridin-3-yl N-oxide | CH₃ | |
| 2.6 | 2,3-di-Cl-pyridin-5-yl | CH₃ | |
| 2.7 | 2-CH₃-pyridin-5-yl | CH₃ | |
| 2.8 | 2-Cl-thiazol-5-yl | C₂H₅ | |
| 2.9 | 6-Cl-pyridin-3-yl | C₂H₅ | |
| 2.10 | 6-Cl-pyridin-3-yl | cyclopropyl | |
| 2.11 | 2-Cl-thiazol-5-yl | cyclopropyl | |

Formulation Examples (%=percent by weight)

| Example F1: Emulsion concentrates | a) | b) | c) |
|---|---|---|---|
| Active ingredient No. 1.2 | 25% | 40% | 50% |
| Calcium dodecylbenzene sulfonate | 5% | 8% | 6% |
| Castor oil polyethylene glycol ether (36 mol of EO) | 5% | — | — |
| Tributylphenol polyethylene glycol ether (30 mol of EO) | — | 12% | 4% |
| Cyclohexanone | — | 15% | 20% |
| Xylene mixture | 65% | 25% | 20% |

Emulsions of any desired concentration can be prepared from such concentrates by dilution with water.

| Example F2: Solutions | a) | b) | c) | d) |
|---|---|---|---|---|
| Active ingredient No. 1.3 | 80% | 10% | 5% | 95% |
| Ethylene glycol monomethyl ether | 20% | — | — | — |
| Polyethylene glycol MW 400 | — | 70% | — | — |
| N-Methyl-2-pyrrolidone | — | 20% | — | — |
| Epoxidised coconut oil | — | — | 1% | 5% |
| Petroleum spirit (boiling range 160–190° C.) | — | — | 94% | — |

The solutions are suitable for use in the form of microdrops.

| Example F3: Granules | a) | b) | c) | d) |
|---|---|---|---|---|
| Active ingredient No. 1.2 | 5% | 10% | 8% | 21% |
| Kaolin | 94% | — | 79% | 54% |
| Highly-disperse silica | 1% | — | 13% | 7% |
| Attapulgite | — | 90% | — | 18% |

The active ingredient is dissolved in dichloromethane, the solution is sprayed onto the carrier, and the solvent is subsequently evaporated in vacuo.

| Example F4: Dusts | a) | b) |
|---|---|---|
| Active ingredient No. 1.2 | 2% | 5% |
| Highly-disperse silica | 1% | 5% |
| Talc | 97% | — |
| Kaolin | — | 90% |

Ready-to-use dusts are obtained by intimately mixing the carriers with the active ingredient.

| Example F5: Wettable powders | a) | b) | c) |
|---|---|---|---|
| Active ingredient No. 1.2 | 25% | 50% | 75% |
| Sodium ligninsulfonate | 5% | 5% | — |
| Sodium lauryl sulfate | 3% | — | 5% |
| Sodium diisobutylnaphthalene-sulfonate | — | 6% | 10% |
| Octylphenol polyethylene glycol ether (7–8 mol of EO) | — | 2% | — |
| Highly-disperse silica | 5% | 10% | 10% |
| Kaolin | 62% | 27% | — |

The active ingredient is mixed with the additives, and the mixture is ground thoroughly in a suitable mill. This gives wettable powders which can be diluted with water to give suspensions of any desired concentration.

| Example F6: Emulsion concentrate | |
|---|---|
| Active ingredient No. 1.3 | 10% |
| Octylphenol polyethylene glycol ether (4–5 mol of EO) | 3% |
| Calcium dodecylbenzene sulfonate | 3% |
| Castor oil polyglycol ether (36 mol of EO) | 4% |
| Cyclohexanone | 30% |
| Xylene mixture | 50% |

Emulsions of any desired concentration can be prepared from this concentrate by dilution with water.

| Example F7: Dusts | a) | b) |
|---|---|---|
| Active ingredient No. 1.2 | 5% | 8% |
| Talc | 95% | — |
| Kaolin | — | 92% |

Ready-to-use dusts are obtained by mixing the active ingredient with the carrier and grinding the mixture on a suitable mill.

| Example F8: Extruder granules | |
|---|---|
| Active ingredient No. 1.3 | 10% |
| Sodium ligninsulfonate | 2% |
| Carboxymethylcellulose | 1% |
| Kaolin | 87% |

The active ingredient is mixed with the additives, and the mixture is ground and moistened with water. This mixture is extruded, granulated and subsequently dried in a stream of air.

| Example F9: Coated granules | |
|---|---|
| Active ingredient No. 1.2 | 3% |
| Polyethylene glycol (MW 200) | 3% |
| Kaolin | 94% |

In a mixer, the finely ground active ingredient is applied uniformly to the polyethylene glycol, which has been moistened with kaolin. Dust-free coated granules are obtained in this manner.

| Example F10: Suspension concentrate | |
|---|---|
| Active ingredient No. 1.3 | 40% |
| Ethylene glycol | 10% |
| Nonylphenol polyethylene glycol ether (15 mol of EO) | 6% |
| Sodium ligninsulfonate | 10% |
| Carboxymethylcellulose | 1% |
| 37% aqueous formaldehyde solution | 0.2% |
| Silicone oil in the form of a 75% aqueous emulsion | 0.8% |
| Water | 32% |

The finely ground active ingredient is mixed intimately with the additives. This gives a suspension concentrate from which suspensions of any desired concentration can be prepared by dilution with water.

Biological Examples (%=percent by weight unless otherwise indicated)

Example B1

Activity against *Anthonomus grandis*

Young cotton plants are sprayed with an aqueous emulsion spray mixture comprising 400 ppm of active ingredient. After the spray coating has dried on, the plants are populated with 10 adult *Anthonomus grandis* and placed into a plastic container. 3 days later, the test is evaluated. The percentage reduction in population and the percentage reduction in feeding damage (% activity) are determined by comparing the number of dead beetles and the feeding damage between the treated and the untreated plants.

In this test, compounds of Tables 1 and 2 exhibit good activity. In particular, compounds No. 1.2, 1.3 and 2.3 exhibit an activity of over 80%.

Example B2

Activity against *Aphis craccivora*

Pea seedlings are infected with *Aphis craccivora*, subsequently sprayed with a spray mixture comprising 400 ppm of active ingredient and then incubated at 20° C. The test is evaluated after 3 and 6 days. The percentage reduction in population (% activity) is determined by comparing the number of dead aphids on the treated and untreated plants.

In this test, compounds of Tables 1 and 2 exhibit good activity. In particular, compounds No. 1.2, 1.3, 1.15, 2.2 and 2.3 exhibit an activity of over 80%.

Example B3

Activity against *Bemisia tabaci*

Dwarf bean plants are placed into gauze cages and populated with adult *Bemisia tabaci*. After oviposition, all adults are removed. 10 days later, the plants together with the nymphs are sprayed with an aqueous emulsion spray mixture comprising 400 ppm of the active ingredient. After a further 14 days, the percentage hatching rate of the eggs is evaluated by comparison with untreated control batches.

In this test, compounds of Tables 1 and 2 exhibit good activity. In particular, compounds No. 1.2 and 1.3 exhibit an activity of over 80%.

Example B4

Activity against *Ctenocephalides felis* (systemic)

Twenty adult fleas of the species *Ctenocephalides felis* are placed into a flat, round cage, both sides of which are covered with gauze. A container whose bottom is sealed with a Parafilm membrane is placed onto the cage. In the container there is blood which comprises 5 ppm of active ingredient and which is constantly heated at 37°. The fleas take up blood through the membrane. The test is evaluated 24 and 48 hours after setting up the experiment. The percentage reduction in population (% activity) is determined by comparing the number of dead fleas when using treated and untreated blood. 24 hours after the treatment, the blood is replaced by fresh blood which has also been treated.

In this test, compounds of Tables 1 and 2 exhibit good activity. In particular, compounds No. 1.2 and 1.3 exhibit an activity of over 80%.

Example B5

Activity against *Diabrotica balteata*

Maize seedlings are sprayed with an aqueous emulsion spray mixture comprising 400 ppm of active ingredient. After the spray coating has dried on, the seedlings are populated with 10 *Diabrotica balteata* larvae in the second stage and transferred to a plastic container. The test is evaluated after 6 days. The percentage reduction in population (% activity) is determined by comparing the number of dead larvae between the treated and untreated plants.

In this test, compounds of Tables 1 and 2 exhibit good activity. In particular, compounds No. 1.2, 1.3, 1.5 and 2.3 exhibit an activity of over 80%.

Example B6

Activity against *Heliothis virescens*

Young soyabean plants are sprayed with an aqueous emulsion spray mixture comprising 400 ppm of active ingredient. After the spray coating has dried on, the plants are populated with 10 *Heliothis virescens* caterpillars in the first stage and transferred to a plastic container. The test is evaluated after 6 days. The percentage reduction in population and in feeding damage (% activity) are determined by comparing the number of dead caterpillars and the feeding damage between the treated and untreated plants.

In this test, compounds of Tables 1 and 2 exhibit good activity. In particular, compounds No. 1.2 and 1.3 exhibit an activity of over 80%.

Example B7

Activity against *Heliothis virescens* (ovi-/larvicidal)

*Heliothis virescens* eggs laid on cotton are sprayed with an aqueous emulsion spray mixture comprising 400 ppm of active ingredient. After 8 days, the percentage hatching rate of the eggs and the survival rates of the caterpillars are evaluated by comparison with untreated control batches (% reduction in population).

In this test, compounds of Tables 1 and 2 exhibit good activity.

Example B8

Activity against *Myzus persicae*

Pea seedlings are infected with *Myzus persicae*, subsequently sprayed with a spray mixture comprising 400 ppm of active ingredient and then incubated at 200. The test is evaluated after 3 and 6 days. The percentage reduction in population (% activity) is determined by comparing the number of dead aphids on the treated and untreated plants.

In this test, compounds of Tables 1 and 2 exhibit good activity. In particular, compounds No. 1.2 and 1.3 exhibit an activity of over 80%.

Example B9

Activity against *Myzus persicae* (systemic)

Pea seedlings are infected with
Myzus persicae, subsequently placed with their roots into a spray mixture comprising 400 ppm of active ingredient and then incubated at 20°. The test is evaluated after 3 and 6 days. The percentage reduction in population (% activity)

is determined by comparing the number of dead aphids on the treated and untreated plants.

In this test, compounds of Tables 1 and 2 exhibit good activity. In particular, compounds No. 1.2, 1.3 and 1.5 exhibit an activity of over 80%.

Example B10

Activity against *Nephotettix cincticeps*

Rice plants are sprayed with an aqueous emulsion spray mixture comprising 400 ppm of active ingredient. After the spray coating has dried on, the plants are populated with larvae in the 2nd and 3rd stages. The test is evaluated after 21 days. The percentage reduction in population (% activity) is determined by comparing the number of surviving leaf hoppers on the treated and untreated plants.

In this test, compounds of Tables 1 and 2 exhibit good activity. In particular, compounds No. 1.2, 1.3 and 1.5 exhibit an activity of over 80%.

Example B11

Activity against *Nephotettix cincticeps* (systemic)

Pots containing rice plants are placed into an aqueous emulsion solution comprising 400 ppm of active ingredient. The plants are subsequently populated with larvae in the 2nd and 3rd stages. The test is evaluated after 6 days. The percentage reduction in population (% activity) is determined by comparing the number of leaf hoppers on the treated and untreated plants.

In this test, compounds of Tables 1 and 2 exhibit good activity. In particular, compounds No. 1.3, 1.5, 1.13 and 1.15 exhibit an activity of over 80%.

Example B12

Activity against *Nilaparvata lugens*

Rice plants are sprayed with an aqueous emulsion spray mixture comprising 400 ppm of active ingredient. After the spray coating has dried on, the plants are populated with plant hopper larvae in the 2nd and 3rd stages. The test is evaluated after 21 days. The percentage reduction in population (% activity) is determined by comparing the number of surviving plant hoppers on the treated and untreated plants.

In this test, compounds of Tables 1 and 2 exhibit good activity. In particular, compounds No. 1.2, 1.3, 1.5, 1.8 and 2.3 exhibit an activity of over 80%.

Example B13

Activity against *Nilaparvata lugens* (systemic)

Pots containing rice plants are placed into an aqueous emulsion solution comprising 10 ppm of active ingredient. The plants are subsequently populated with larvae in the 2nd and 3rd stages. The test is evaluated after 6 days. The percentage reduction in population (% activity) is determined by comparing the number of plant hoppers on the treated and untreated plants.

In this test, compounds of Tables 1 and 2 exhibit good activity. In particular, compounds No. 1.2, 1.3, 1.4, 1.5, 1.13, 1.15, 2.2 and 2.3 exhibit an activity of over 80%.

Example B14

Action against *Blattella germanica*

A solution (0.1%) of the active ingredient in acetone is placed into a Petri dish in such an amount that this corresponds to an application rate of 1 g/m$^2$. When the solvent has evaporated, 10 nymphs of *Blattella germanica* (last nymphal stage) are placed in the dish and exposed to the action of the test substance over 2 hours. The nymphs are then anaesthetised using $CO_2$, transferred to a fresh Petri dish and kept in the dark at 25° and circa 70% atmospheric humidity. After 48 hours, the insecticidal action is determined by calculating the destruction rate.

In this test, compounds of Tables 1 and 2 exhibit good activity. In particular, compound No. 1.3 exhibits an activity of over 80%.

Example B15

Action against *Lucilia cuprina*

Batches of 30 to 50 freshly deposited eggs of *Lucilia cuprina* are placed in test tubes in which 4 ml of nutrient medium have previously been mixed with 1 ml of test solution comprising 16 ppm of active ingredient. After inoculation of the culture medium, the test tubes are sealed with a cotton wool plug and incubated in the incubator for 4 days at 30°. Up to this point in time, larvae approximately 1 cm in length (stage 3) develop in the untreated medium. If the test substance is active, then the larvae are either dead or their development is clearly slowed down at this point in time. The test is evaluated after 96 hours.

In this test, compounds of Tables 1 and 2 exhibit good activity. In particular, compound No. 1.3 exhibits an activity of over 80%.

Example B16

Action against *Musca domestica*

A sugar lump is treated with such an amount of test substance solution that the concentration of test substance in the sugar is 250 ppm after drying overnight. The lump which has been treated in this manner is placed on an aluminium dish together with a wet cotton wool ball and 10 adults of an OP-resistant strain of *Musca domestics*. The dish is covered with a glass beaker and incubated at 25°. The mortality rate is determined after 24 hours.

In this test, compounds of Tables 1 and 2 exhibit good activity. In particular, compound No. 1.3 exhibits an activity of over 80%.

What is claimed is:

1. Pest-resistant plant propagation material comprising plant propagation material selected from the group consisting of seeds and plant cuttings treated with a pesticidally effective amount of a pesticidal composition, wherein said pesticidal composition comprises a pesticidally effective amount of a pesticidally active ingredient in an inert carrier, said pesticidally active ingredient being selected from the group, consisting of a compound of the formula $$A\diagdown N\diagup\overset{O}{\underset{X}{\diagdown N\diagup}}\diagdown R, \quad (I)$$

an agrochemically utilizable salt of said compound of the formula I, a tautomer of said compound of the formula I, and an agrochemically utilizable salt of said tautomer, wherein in formula I A is a 2-chloropyrid-5-yl, 2-methylpyrid-5-yl, 1-oxido-3-pyridinio, 2-chloro-1-oxido-5-pyridinio, 2,3-dichloro-1-oxido-5-pyridinio or 2-chlorothiazol-5-yl group, R is hydrogen, $C_1$–$C_6$alkyl, phenyl-$C_1$–$C_4$alkyl, $C_3$–$C_6$cycloalkyl, $C_2$–$C_6$alkenyl or $C_2$–$C_6$alkynyl; and X is N—$NO_2$ or N—CN.

2. The pest-resistant plant propagation material of claim 1, wherein the seed is a fruit, tuber or kernel.

3. The pest-resistant plant propagation material of claim 1, wherein R is $C_1$–$C_6$alkyl, phenyl-$C_1$–$C_4$alkyl, $C_3$–$C_6$cycloalkyl, $C_3$–$C_4$alkenyl or $C_3$–$C_4$alkynyl.

4. The pest-resistant plant propagation material of claim 1, wherein X is N—$NO_2$.

5. The pest-resistant plant propagation material of claim 1, wherein A is a 2-chlorothiazol-5-yl or 2-chloropyrid-5-yl group, R is $C_1$–$C_4$alkyl and X is N—$NO_2$.

6. The pest-resistant plant propagation material of claim 5, wherein the pesticidally active ingredient is 5-(2-chloropyrid-5-ylmethyl)-3-methyl-4-nitroiminoperhydro-1,3,5-oxadiazine.

7. The pest-resistant plant propagation material of claim 5, wherein the pesticidally active ingredient is 5-(2-chlorothiazol-5-ylmethyl)-3-methyl-4-nitroiminoperhydro-1,3,5-oxadiazine.

8. The pest-resistant plant propagation material of claim 1, wherein the pesticidally active ingredient is 3-methyl-4-nitroimino-5-(1-oxido-3-pyridiniomethyl)-perhydro-1,3,5-oxadiazine.

9. The pest-resistant plant propagation material of claim 1, wherein the pesticidally active ingredient is 5-(2-chloro-1-oxido-5-pyridiniomethyl)-3-methyl-4-nitroimino-perhydro-1,3,5-oxadiazine.

10. The pest-resistant plant propagation material of claim 1, wherein the pesticidally active ingredient is 3-methyl-5-(2-methylpyrid-5-ylmethyl)-4-nitroimino-perhydro-1,3,5-oxadiazine.

* * * * *